United States Patent [19]

Shaw

[11] Patent Number: 4,480,031

[45] Date of Patent: Oct. 30, 1984

[54] REPLICATOR WITH SLIDABLE PINS

[76] Inventor: Joseph R. H. Shaw, 231 Arundel Ave., St. Paul, Minn. 55102

[21] Appl. No.: 446,258

[22] Filed: Dec. 2, 1982

Related U.S. Application Data

[63] Continuation of Ser. No. 317,177, Nov. 2, 1981, abandoned.

[51] Int. Cl.³ .................. C12Q 1/00; C12M 1/20; C12M 1/26
[52] U.S. Cl. ...................................... 435/30; 435/292
[58] Field of Search .................................. 435/30, 292

[56] References Cited

U.S. PATENT DOCUMENTS 3,455,788  7/1969  Curry ........................... 435/30 X
4,042,463  8/1977  Haque ........................... 435/30 X
4,115,200  9/1978  Anderson ....................... 435/30 X

FOREIGN PATENT DOCUMENTS 2917180  11/1979  Fed. Rep. of Germany ........ 435/30

*Primary Examiner*—Sidney Marantz

[57] ABSTRACT

A replicator (10) having an impregnation head (32) utilizing a plurality of floating pins (42) is the subject of this patent application. The pins (42) extend slidably through a platen (34) of the head (32) so that, as lower ends of the pins (42) engage an upper surface (24) of a test medium (14) to deposit broths (20) containing test isolates thereon, the pins (42) will slide upwardly relative to the platen (34) so that recesses are not formed in the surface (24) of the test medium (14).

10 Claims, 3 Drawing Figures

REPLICATOR WITH SLIDABLE PINS

This is a continuation of application Ser. No. 317,177, filed Nov. 2, 1981, now abandoned.

TECHNICAL FIELD

The invention of the present application deals broadly with the technology whereby testing and analysis of liquid materials such as broths innoculated with disease causing organisms from clinical isolates are transferred from a tray having a plurality of wells, each containing a different broth, to a media plate having an identification medium or an antimicrobic by which the susceptibility characteristics of the organism can be measured. The invention includes structure whereby recesses are not formed in the identification medium or antimicrobic in the recipient tray by a plurality of innoculating pins which are dipped into the broths and made to engage the upper surfaces of the media in the recipient trays.

BACKGROUND OF THE INVENTION

Laboratories, and particularly hospital laboratories, conduct tests on various liquid materials, such as disease causing organisms, isolated from the system of an infected patient. Such testing typically requires that many substantially similar tests be performed on small samples of the clinical isolates. Similarly, such testing may require the exposure of a large number of isolates taken from different patients to a single particular test medium in order to determine which of the samples contains a particular disease causing organism or which of the samples is susceptible to a single particular antimicrobic.

Such testing is exact and time consuming work. Consequently, it is particularly desirable if a large number of specimens can be simultaneously applied to a single test medium or antimicrobic in order to minimize the man hours of skilled laboratory technicians necessary to conduct all tests with respect to a fixed group of clinical isolates.

Various structures have been designed to facilitate this transfer and exposure of a plurality of isolates to the test medium. One such structure is illustrated in Canadian Pat. No. 990,101 issued to Berend C. deKat on June 1, 1976. The structure of that patent is referred to in the trade as a replicator inoculating device. Such devices typically include a base structure and a support pillar to which a transport mechanism is rotatably coupled. The transport mechanism includes a plurality of downwardly extending pins.

The base plate carries a multiple well container, at one end thereof, and a receiving tray, at the opposite end. The multiple well container is keyed to the base plate to make it orientable whereby each of the pins carried by the transport mechanism can, when the mechanism is in a position directly above the well container, enter one of the wells. The mechanism can, thereafter, be moved to a second position wherein the pins are made to engage the surface of a test medium or antimicrobic reagent. An amount of the broth containing the disease causing organism from the clinical isolate can, thereby, be deposited on the surface of the medium or reagent.

The transport mechanism is typically structured so that the pins extend generally vertically regardless of the positioning of the transport mechanism with respect to the multiple well container and receiving tray. The small amounts of the broths adhering to lower portions of the pins as a result of the pins being partially immersed in the liquids disposed in each of the wells will be facilitated in running off of the surfaces of the pins and onto the medium or reagent.

Generally, however, the amount of the broth which adheres to each pin is sufficiently small and surface tension is sufficiently great so that the broth will not drain onto the medium unless the pins are made to engage the surface thereof. It is, however, desirable that the surface of the medium be maintained uniformly flat. This is so since accurate determinations cannot be made unless contamination of one of the broths by another is precluded. Additionally, best results are achieved when the broth is applied to the medium in a fine film rather than puddled in a small indentation which can be formed in the surface of the medium if too much pressure is applied thereto by the transport mechanism and the pins carried thereby.

It is to this shortcoming in the prior art that the invention of the present application is directed. The IMPROVED REPLICATION of this application provides structure which minimizes the likelihood of indentations being formed in the surfaces of the medium and facilitates the application of the broths in the desired film form.

SUMMARY OF THE INVENTION

The invention of the present application is an improved replicator for inoculating identification media and antimicrobics with a broth containing disease causing organisms from clinical isolates and a process for accomplishing such inoculation. The innovative features of the replicator apparatus are directed to the impregnation head of the replicator. The apparatus includes at least one pin. The pin includes an axis of elongation which is oriented generally vertically, and the pin is disposed for vertical movement. The at least one pin is normally biased to a lower position. The pin has a lower end which is capable of carrying a small amount of a disease causing organism broth on its outer surface. When the pin is lowered so that its lower end engages an upwardly facing surface of the culture medium or antimicrobic, the pin is urged upwardly overcoming its bias. The upper surface of the medium carried in a plate or dish is thereby protected against pitting and pocking.

Biasing of the pins downwardly can be accomplished in a number of ways. In a preferred embodiment, however, the pins are biased downwardly by gravity.

The impregnation head is suitable to be carried by a replicator of the type having in inoculating arm for transferring disease causing organism broths from a tray to the test medium. In one type of such a replicator, the tray has a multiplicity of wells patterned therein. Each of the wells can contain a different liquid isolate. Many isolates can, thereby, be transferred and applied to the test medium in a film so that each isolate can be tested for the same properties.

With such a replicator embodiment, the impregnation or transfer head includes a carrier plate mountable to a support carried by the inoculating arm. The arm can be pivotable between positions wherein the support is disposed above the tray and wherein it is disposed above the test medium dish. The carrier plate is, thereby, moved between these positions.

Rather than using a single pin, the plate can carry a multiplicity of pins which extend through apertures formed in the plate. The pins can be spaced about the plate so that they form a pattern sized and shaped to approximate a pattern formed by the wells in the trade. When the plate is in its first position, therefore, each of the pins can extend downwardly with a lower end thereof immersed in the broth carried by one of the wells.

The pins can slide readily through the apertures in the plate so that, when the innoculating arm is moved to its second position with the carrier plate above the test medium dish with lower ends of the pins engaging the upper surface of the test medium, the pins will be allowed to slide upwardly relative to the plate so that they do not form pits in the surface of the test medium.

The invention of the present application is, therefore, an apparatus and method for alleviating certain deficiencies in the prior art wherein the broth carrying a disease causing organism was allowed to puddle on the surface of the test medium. More specific advantages of the invention will become apparent with reference to the detailed description of the invention, claims, and appended drawings.

DETAILED DESCRIPTION OF THE INVENTION

Figure 1:
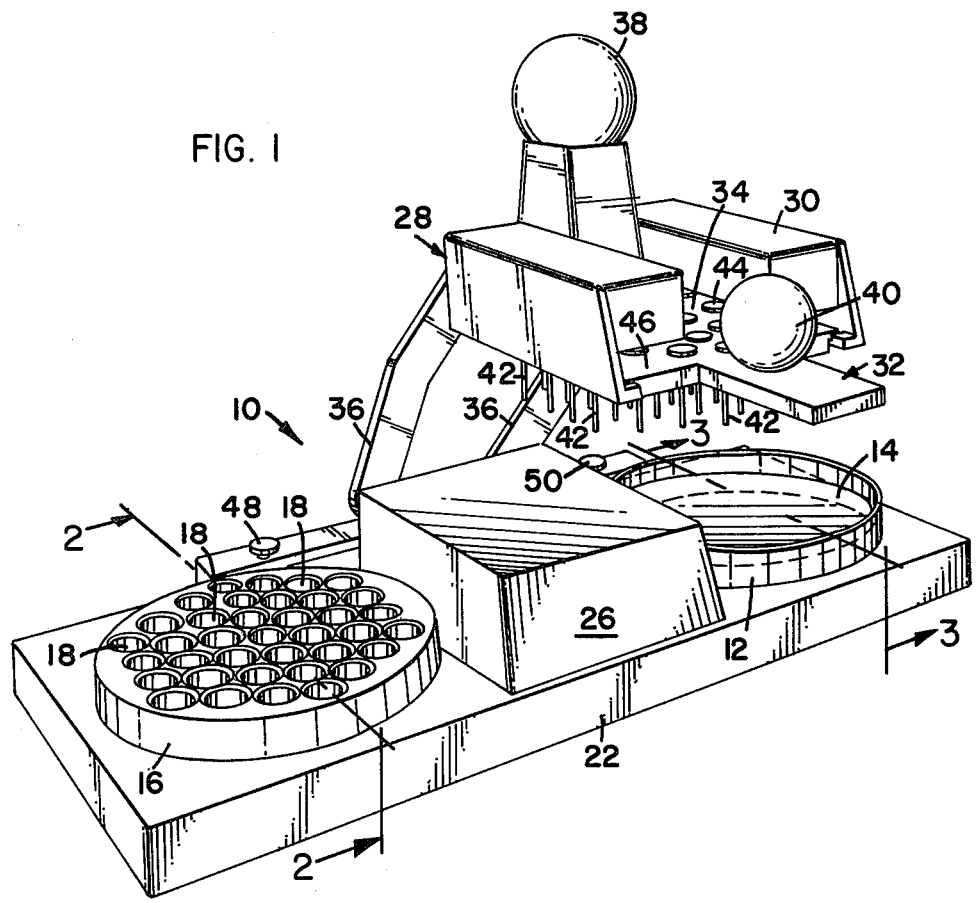
FIG. 1 is a view in perspective illustrating a replicator with which the invention of the present application can be used and showing the impregnation head mounted in the support of the inoculating arm.

Referring now to the drawings wherein like reference numerals denote like elements throughout the several views, FIG. 1 illustrates an improved replicator device 10 for transferring a multiplicity of different disease causing organism broths to a single dish 12 or tray containing an identification or antimicrobic medium 14. A seeding tray 16 is shown as having a multiplicity of wells 18 formed therein, each of the wells 18 containing one of the disease causing organism broths 20.

Although not essential to the invention, the tray 16 can be configured with 37 wells 18 formed therein in a closed hexagonal pattern. In one particular replicator structure, the seeding tray 16 is keyed to a base plate 22 in order to orient the tray 16 relative thereto in a particular manner. The keying precludes rotation of the tray 16 within a recess formed in the base plate 22.

In order to provide a frame of reference on a test medium 14 to which the broths 20 are transferred, one of the wells 18 can be filled with a dye. Typically, a well 18 at one of the apexes of the hexagon would contain the dye. When the broths 20 and dye are transferred to the test medium 14 in a manner to be defined hereinafter, the particular broths 20 inoculated onto the surface of the medium 14 can be identified by comparing the location of a particular point of inoculation on the medium surface 24 to the point of inoculation of the dye. It is assumed, of course, that one particular well 18 is, by convention, utilized as the well which is filled with the dye and that the particular well in the seeding tray 16 in which a particular broth 20 is placed is known and recorded.

The tray 16 containing the test medium 14, which can be an identification reagent or an antimicrobic agar medium, is positioned at the opposite end of the base plate 22. A barrier 26 can be provided between the seeding tray 16 and the test medium dish or plate 12. The barrier 26 can serve to prevent inadvertent inoculating of the medium 14 by one or more of the broths 20 contained in the wells 18.

The replicator 10 is shown as having mounted, proximate the rear end of the base plate 22, a transport or inoculating arm 28. The arm 28 includes a transfer head support 30 which is disposed to seatably receive a transfer or impregnation head 32 thereon. The support 30 is configured so that a platen or plate like structure 34 of the head carried by the support 30 is maintained so as to define a generally horizontal plane. To this end, the arm 28 can include two generally parallely extending elements 36, each element 36 being pivotally mounted, at a lower end thereof, at the back of replicator 10, and at an upper end thereof, to the transfer head support 30. The elements 26 are made similar in length, and the respective attachment points at the replicator 10 and the transfer head support 30 are positioned relative to one another to define generally horizontal planes. Such an arrangement of parts affords a structure wherein the impregnation head 32, when seated upon the support 30, will be maintained in its generally horizontal orientation.

Figure 2:
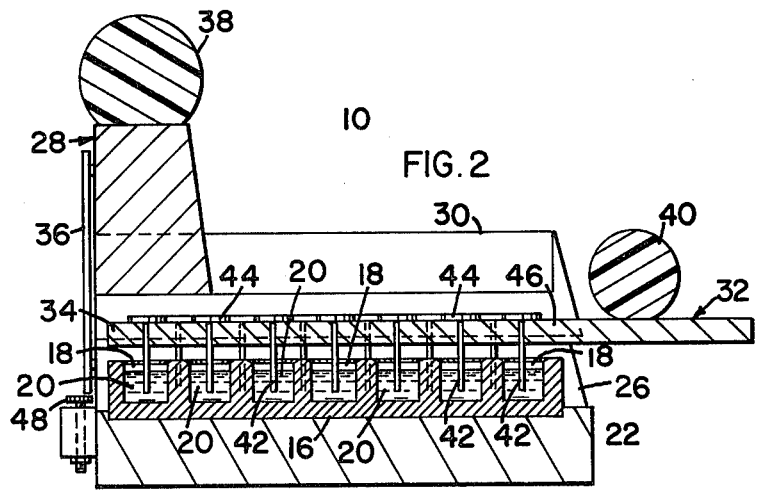
FIG. 2 is a side sectional view of the replicator of FIG. 1 taken generally along the line 2—2 of FIG. 1, but with the inoculating arm in its first position.
Figure 3:
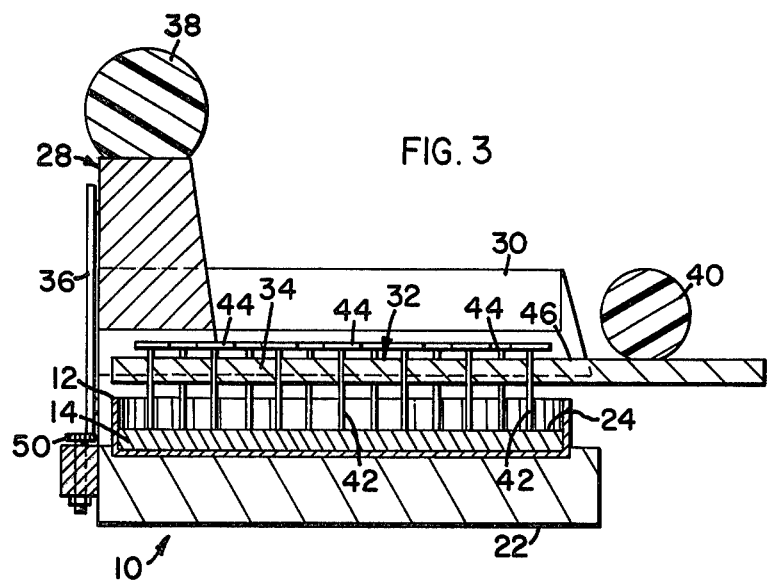
FIG. 3 is a side sectional view of the replicator of FIG. 1 taken generally along the line 3—3 of FIG. 1, but with the inoculating arm in its second position with lower ends of the pins engaging the upper surface of the test medium.

With a replicator so configured, the impregnation head 32, along with the transport arm 28, can be moved from a first position immediately above the seeding tray 16 (as seen in FIG. 2) to a second position immediately above the test medium dish 12 (as seen in FIG. 3). In order to facilitate movement of the head 32 between its respective first and second positions, a grasping handle can be provided. As seen in FIG. 1, the handle can include a spherical member 38 which is both easily graspable by the hand and aesthetically pleasing. Similarly, the impregnation head 32 can be provided with a spherical member 40 by which the head 32 can be held while seating it upon and removing it from the transport arm support 30.

The figures illustrate a multiplicity of pins 42 extending through apertures formed in the platen 34. It will be understood that, although the figures illustrate a structure intended to carry 37 pins 42, lesser numbers of pins 42 can be utilized.

In any case, however, regardless of the number of pins 42 which are, in fact, used, each of the pins 42 will extend into one of the wells 18 formed in the seeding tray 16 when the transport arm 28 is moved so that the impregnation head 32 is in its first position.

As previously indicated, the specific replicator illustrated is designed to utilize 37 pins 42. When such a number is used, the pins 42 can be patterned in a hexagonal shape of a size so that each of the pins will extend into one of the wells 18 in the seeding tray 16 when the impregnation head 32 is in its first position.

Although not essential to the invention, the pins 42 are shown as extending generally vertically; that is, substantially transverse to a plane defined by the head 32. The pins 42 are structured, in such an embodiment, so that they have a generally vertically extending axis of elongation. Typically, a horizontal cross section of such a vertically extending pin 42 would be circular as would be the aperture formed in the platen 34 through which the pin 42 extends. The diameter of each aperture would be slightly greater than that of the pin 42 extending therethrough. As a result, the pin 42, while being maintained in its vertical orientation, will be allowed to float freely in a vertical direction with respect to the platen 34.

Each pin 42 is illustrated as having a movement limiting cap 44 formed at the top end thereof. Such a cap 44 precludes the pin 42 from slipping out of the aperture, thereby limiting the downward relative movement of the pin 42 with respect to the platen 34.

The pins 42 are biased downwardly relative to the platen 34 so that the caps 44 will sit on an upper surface 46 of the platen 34. Although positive biasing means can be included, typically, the weights of the pins 42 are sufficient to maintain the pins 42 with their caps 44 seated on the platen 34. Fixed positions which the pins 42 normally occupy are defined by the pins 42 with their caps 44 seated on the platen 34.

Referring now to FIG. 2, a stop 48 can limit movement of the impregnation head 32 toward the seeding tray 16 so that the first position of the head 32 will be defined with the head 32 spaced slightly vertically from the tray 16. The pin or pins 42 are given lengths such that, when the head 32 is in its first position, they will extend sufficiently downward so that lower ends thereof will be immersed in broths 20 contained in the wells 18. When the impregnation head 32 is maneuvered to its second position, as illustrated in FIG. 3, small amounts of the broths 20 will adhere to the pins 42.

As the transport arm 28 is maneuvered to position the impregnation head 32 in its second position, amounts of the broths 20 will remain adhering to the lower ends of the pins 42. Although as in the case of the first position of the head 32, a stop 50 limits motion of the impregnation head 32 toward the test medium dish 12 so that, in its second position, the head 32 is spaced slightly vertically above the test medium 14, the pins 42 extend sufficiently far below the platen 34 so that their lower ends will engage an upper surface 24 of the medium 14. With the impregnation head 32 in its second position, therefore, the small amount of broths 20 adhering to the pins 42 will be deposited on the upper surface 24 of the test medium 14. Since the pins 42 are, however, free to float upwardly relative to the platen 34 upon engagement of the lower ends thereof with the test medium 14, pitting and pocking of the surface 24 of the medium 14 by the pins 42 will be prevented. Consequently, the broths 20 will be applied to a smooth surface in the form of a fine film rather than being allowed to puddle in recesses which might otherwise be formed in the surface 24 of the medium 14 by engagement by the pins.

As previously indicated, the location of each particular broth 20 can be ascertained because of the known position of the well 18 in which it was contained relative to the well containing the dye. After a period of incubation, results of the manner of reaction of a particular broth 20 in the environment of the particular test medium 14 can be ascertained.

It will be understood that in many instances in this application specific embodiments and desireable structures for practicing the invention are disclosed. The scope of the invention, however, is defined in the language in which the appended claims are expressed, and structures might be built which, although diverging in some respects from the structure of a particularly desirable embodiment described in this detailed description, do not exceed the scope of the invention.

What is claimed is:

1. In combination with a replicator device having a transport arm carrying a support movable between a first position immediately above a tray having a plurality of liquid containable wells patterned therein, and a second position immediately above a test medium plate spaced laterally from the tray; a transfer head seatable on the support, the head comprising:

(a) a platen having a plurality of apertures formed therethrough, said apertures formed in a pattern sized and shaped similarly to the pattern formed by the wells in the tray; and (b) a plurality of pins, each of said pins extending through one of said apertures and sized relative thereto to permit free movement relative to said platen.

2. The combination of claim 1 further comprising means for limiting movement of said pins relative to said platen, in a direction toward the test medium plate, beyond fixed positions.

3. The combination of claim 2 wherein said platen defines a generally horizontal plane and wherein said pins move generally vertically relative to said platen, said movement limiting means comprising a cap carried by each pin at a top end thereof, whereby relative movement of each of said pins in a downward direction is precluded when said cap engages said platen.

4. The combination of claim 1 wherein each of said pins has an axis of elongation and is circular in cross-section taken in a plane orthogonal to said axis, and each of said apertures is circular, and wherein the diameter of each of said apertures closely approximates the diameter of said pin extending therethrough.

5. The combination of claim 4 wherein the diameter of each of said apertures is slightly larger than the diameter of said pin extending therethrough.

6. A transfer head suitable to be carried by an inoculating arm of a replicator for transferring disease causing organism broths from a multiplicity of wells patterned in a tray to a test medium dish, spaced laterally from the tray, and depositing them on the medium in a film, comprising:

(a) a carrier plate mountable to the inoculating arm and disposed for movement, along with said arm, between a first position above the tray and a second position above the dish; and (b) a multiplicity of pins slidably extending through said plate and forming a pattern sized and shaped to approximate the pattern formed by the wells, each of said pins having a lower end capable of entering a corresponding well; and (c) wherein said pins slide upwardly relative to said plate when said lower ends of said pins are made to engage a surface of a test medium in the medium dish;

(d) whereby pitting of said surface of the test medium by said pins is impeded.

7. The head of claim 6 further comprising means for preventing said pins from sliding out of said carrier plate as it is moved between said first and said second positions.

8. A culture medium impregnation head, comprising at least one pin disposed for vertical movement and biased to a lower position, said at least one pin having a lower end capable of carrying a small amount of a disease carrying organism broth, wherein, when said lower end engages an upper surface of a culture medium contained in a test medium plate, said at least one pin is urged upwardly to overcome said bias; whereby pocking of said upper surface of said culture medium by engagement by said at least one pin is minimized.

9. The head of claim 8 wherein said at least one pin is biased to said lower position by gravity.

10. A process for preventing pitting of a surface of an identification or antimicrobic test medium to which a test isolate is applied by at least one elongated, generally vertically extending applicator pin; comprising the step of allowing said pin to float upwardly as a lower end thereof engages said surface to apply a film of said test isolate thereto.

* * * * *